United States Patent [19]

Mukohyama et al.

[11] Patent Number: 4,547,571
[45] Date of Patent: Oct. 15, 1985

[54] PROCESS FOR PREPARING CARBOXYMETHYL ETHYL CELLULOSE SUITABLE FOR ENTERIC COATING

[75] Inventors: Hideaki Mukohyama; Ryoichi Hiraoka; Shohachi Ushijima; Motoyasu Saito, all of Yatsushiro, Japan

[73] Assignee: Kohjin Co., Ltd., Tokyo, Japan

[21] Appl. No.: 657,865

[22] Filed: Oct. 5, 1984

[30] Foreign Application Priority Data

Oct. 6, 1983 [JP] Japan ................... 58-185978
Apr. 18, 1984 [JP] Japan ................... 59-76582

[51] Int. Cl.$^4$ ................... C08B 11/193; C08B 11/08
[52] U.S. Cl. ................... 536/90
[58] Field of Search ................... 536/90

[56] References Cited

U.S. PATENT DOCUMENTS

| | | | |
|---|---|---|---|
| 3,789,117 | 1/1974 | Tsujino ................... | 536/90 |
| 4,250,305 | 2/1981 | Saito et al. ................... | 536/84 |
| 4,311,833 | 1/1982 | Namikoshi et al. ................... | 536/90 |
| 4,456,751 | 6/1984 | Messelt et al. ................... | 536/90 |
| 4,477,657 | 10/1984 | Strange et al. ................... | 536/90 |

*Primary Examiner*—Ronald W. Griffin
*Attorney, Agent, or Firm*—Armstrong, Nikaido, Marmelstein & Kobovcik

[57] ABSTRACT

A process for preparing carboxymethyl ethyl cellulose (CMEC) suitable for enteric coating which comprises (1) adding an alkali metal hydroxide and water to a substantially water-immiscible organic solvent dispersion of carboxymethyl cellulose (CMC) and reacting CMC with an ethyl halide in the presence of a phase transfer catalyst, (2) dissolving the produced CMEC in an aqueous solution of a basic compound selected from the group consisting of ammonia, a water-soluble amine and an alkali metal hydroxide and subjecting the resulting solution to depolymerization in the presence of a peroxide, (3) neutralizing the resulting basic reaction mixture with an acidic substance in the presence of a lower alkyl alcohol or acetone to form a hydrogel of the depolymerized CMEC, subjecting the hydrogel to dehydration with agitation, isolating the depolymerized CMEC and washing with water, and (4) drying the wet depolymerized CMEC without pulverization or after pulverizing in the wet state to particles having an average particle size of at most 100 μm. The product has an excellent quality, and is easily soluble in organic solvents and easily dispersible in water, and provides a coating film having excellent strength, resistance to gastric juice and solubility in intestinal juice. Also, the solubility in organic solvents and dispersibility in water of the product can be controlled by selecting the basic compound used in the depolymerization.

6 Claims, No Drawings

4,547,571

PROCESS FOR PREPARING CARBOXYMETHYL ETHYL CELLULOSE SUITABLE FOR ENTERIC COATING

BACKGROUND OF THE INVENTION

The present invention relates to a process for preparing an improved carboxymethyl ethyl cellulose.

Carboxymethyl ethyl cellulose (hereinafter referred to as "CMEC") is prepared by reacting carboxymethyl cellulose (hereinafter referred to as "CMC") with an etherifying agent such as an ethyl halide in the presence of a caustic alkali. It is known, as disclosed in U.S. Pat. No. 4,250,305, that when a phase transfer catalyst is employed in the reaction, one of the reaction substrates is solubilized in another phase, that is, the reaction system is made more homogeneous, whereby not only poor reproducibility of ethylation owing to heterogeneous reaction in conventional processes is overcome, but also CMEC of high quality having a uniform distribution of ethoxyl substituent group is obtained.

CMEC has been employed in enteric protective coating. The fundamental physical property required for enteric protective coating films is that the films are not dissolved or disintegrated in gastric juice, but are promptly dissolved in intestinal juice. However, in practical use, only satisfaction of such a requirement is insufficient, and it is required that the shrinkability of films at the time of coating and the mechanical properties of coating films are over specific levels. When the shrinkability of film in film formation is large, even if a uniform coating film is formed, the film is easy to locally cause cracks due to stress that the film receives in gastric juice. Even in the case where no change of film is observed in gastric juice for the sake of appearance, the effect of a medicine is easy to be decreased, since gastric juice penetrates through the cracked portion, thus resulting in fault in practical use. On the other hand, it is also necessary to prevent disintegration of the film owing to external stress at the time of coating or on storage, to say nothing that the film is endurable to stress in gastric juice. From such a point of view, insufficiency in mechanical properties, especially tensile strength and elongation, of the obtained film causes a problem in practical use, since the film is subject to disintegration by external stress.

CMEC has a better hydrolysis resistance than cellulose acetate phthalate used conventionally as an enteric coating material, but still causes change during preparation steps or storage, thus forming a gel material nsoluble in a solvent used for preparing an enteric coating solution, lowering the film-forming property, producing cracks in coating films, or lowering the enteric property (namely requiring a longer time in dissolution). The reason is considered to be that ester linkage such as a lactone is produced by heating under acidic condition.

Coating procedure of CMEC can be conducted in the form of an organic solvent solution, but an aqueous coating liquid is desired from the viewpoint of the economy in process step such as recovery of a solvent and the safety. Dispersion of CMEC into water is carried out by mechanically pulverizing CMEC into fine particles and dispersing the fine particles into water with a plasticizer, dispersing agent, etc. The pulverization of CMEC is industrially disadvantageous in that a large power is required in mechanical pulverization of dried CMEC and moreover the obtained powder is hard to handle owing to dusting.

It is an object of the present invention to provide a process for preparing a depolymerized CMEC excellent in strength of the cast film.

A further object of the invention is to provide a process for preparing a depolymerized CMEC which does not cause chemical and physical changes during the preparation and on storage with the lapse of time.

A still further object of the invention is to provide a process for preparing a depolymerized CMEC which is easy to be dissolved in a solvent and is capable of forming a uniform coating film.

Another object of the invention is to provide a process for preparing a depolymerized CMEC suitable for preparation of an aqueous enteric coating liquid, which has a good dispersibility in water and causes scarcely dusting.

These and other objects of the present invention will become apparent from the description hereinafter.

SUMMARY OF THE INVENTION

It has now been found that CMEC having an excellent water dispersibility and is suitable for enteric coating use is obtained by subjecting a dispersion of CMC in a specific organic solvent to which a caustic alkali is added, to etherification with an ethyl halide in the presence of a phase transfer catalyst to produce CMEC, depolymerizing CMEC in an aqueous alkaline solution, neutralizing the reaction mixture with an acid in the presence of a lower alkyl alcohol or a ketone to form a hydrogel of the depolymerized CMEC, heating the hydrogel for dehydration followed by filtration and washing with water, and drying the wet CMEC immediately or after pulverization.

In accordance with the present invention, there is provided a process for preparing carboxymethyl ethyl cellulose suitable for enteric coating which comprises:

(1) adding an alkali metal hydroxide to a dispersion of carboxymethyl cellulose in an organic solvent and subjecting the dispersion to a reaction with an ethyl halide in the presence of a phase transfer catalyst to produce carboxymethyl ethyl cellulose, said carboxymethyl cellulose having a degree of substitution of carboxymethyl group of 0.2 to 1.2, and said organic solvent being substantially immiscible with an aqueous solution of the alkali metal hydroxide and capable of dissolving the ethyl halide, (2) dissolving carboxymethyl ethyl cellulose in an aqueous solution of a basic compound selected from the group consisting of ammonia, a water-soluble amine and an alkali metal hydroxide, and subjecting the resulting solution to depolymerization in the presence of a peroxide, (3) neutralizing the resulting basic solution of the depolymerized carboxymethyl ethyl cellulose with an acidic substance in the presence of an alkyl alcohol having 1 to 3 carbon atoms or acetone to form a hydrogel of carboxymethyl ethyl cellulose, and subjecting the hydrogel to dehydration with agitation at a temperature not lower than the temperature at which dehydration occurs, followed by isolation and washing with water, and (4) drying the wet carboxymethyl ethyl cellolose. If desired. the wet carboxymethyl ethyl cellulose may be pulverized in the wet state to particles having an average particle size of not more than 100 μm, preferably not more than 40 μm before drying.

DETAILED DESCRIPTION

In the first step of the process of the present invention, CMEC is prepared from CMC by dispersing CMC in an organic solvent, adding an alkali metal hydroxide and water to the dispersion and reacting CMC with an ethyl halide in the presence of a phase transfer catalyst. It is important for attaining the objects of the invention to obtain CMEC capable of forming an enteric. strong film and having a uniform distribution of substituent groups. From the viewpoint of the enteric property, CMC having a degree of substitution of carboxymethyl group of 0.2 to 1.2, preferably 0.3 to 0.7, is employed. For obtaining CMEC having a uniform distribution of substituent groups. it is preferable to select CMC having a uniform degree of substitution of carboxymethyl group. The selection of CMC having a uniform degree of substitution can be made by measuring the viscosity of a 2% by weight aqueous solution of CMC at 25° C. by a Brookfield viscometer at 6 r.p.m. and 30 r.p.m. in the number of rotations of the rotor, and selecting CMC showing a ratio of the viscosity at 6 r.p.m. to the viscosity at 30 r.p.m., $\eta_6/\eta_{30}$ (hereinafter referred to as "viscosity ratio"), of not more than 1.3.

Organic solvents which are not miscible with an aqueous solution of an alkali metal hydroxide in all proportions are used as solvents for dispersing CMC. Examples of the organic solvents are, for instance, aliphatic hydrocarbons and aromatic hydrocarbons.

The amount of the organic solvent is from 2 to 6 times the weight of CMC used. CMC is dispersed in the organic solvent, and to the dispersion are added 1 to 4 moles of an alkali metal hydroxide and 1 to 5 moles of water per mole of the hydroxyl group of CMC. At that time, the dispersion of CMC (CMC slurry) is kept at a temperature of 30° to 60° C. and the concentration of the added aqueous alkali solution is adjusted to at least 40 % by weight, whereby blocking of CMC particles can be physically prevented and accordingly the following etherification can be made to proceed more uniformly.

To the thus obtained CMC slurry are added an ethyl halide as an etherifying agent and a quaternary salt as a phase transfer catalyst such as a tetraalkylammonium salt wherein the term "alkyl" means an alkyl group having 1 to 4 carbon atoms or an aralkyl group having 7 to 8 carbon atoms, and the etherification reaction is then carried out. After the completion of the reaction, the produced CMEC is recovered by removing the solvent, neutralizing the excess alkali with a mineral acid such as sulfuric acid, washing with water and drying.

The ethyl halide used in the etherification includes, for instance, ethyl chloride and ethyl bromide. and the use of ethyl chloride is particularly preferable. Preferably, the ethyl halide is employed in an amount of at least 1.2 moles, especially at least 2 moles, per mole of the hydroxyl group of CMC.

Quaternary ammonium salts wherein a $C_1$ to $C_4$ alkyl group and/or a $C_7$ to $C_8$ aralkyl group are bonded to nitrogen atom, are used as phase transfer catalysts in the etherification reaction. Representative examples are, for instance, tetramethylammonium chloride, tetraethylammonium chloride and benzyltriethylammonium chloride. Quaternary phosphonium salts such as tetraethylphosphonium chloride are also usable in the present invention as a phase transfer catalyst. The amount of the phase transfer catalyst is from 0.1 to 20% by mole based on the hydroxyl group of CMC.

The quaternary ammonium salt may be formed in situ during the etherification. Any compounds which ultimately form or produce quaternary ammonium salts in the reaction system, are usable as phase transfer catalysts in the invention, e.g. compounds capable of forming quaternary ammonium salts by reaction with an excess etherifying agent, such as ammonia and primary, secondary and tertiary amines of the formula:

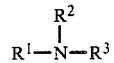

wherein $R^1$, $R^2$ and $R^3$ are hydrogen, an alkyl group having 1 to 4 carbon atoms or an aralkyl group having 7 to 8 carbon atoms.

The etherification reaction is carried out at a temperature of 100° to 150° C., preferably 110° to 120° C. The reaction time varies depending on the kinds of quaternary ammonium or phosphonium salt and ethyl halide and the reaction temperature, but about 7 to about 15 hours are sufficient.

According to the present invention, the reaction system forms a good slurry system, and blocking of the reactants which is one of the defects seen in the case of not using the quaternary salt, does not occur. Accordingly, it is possible to conduct the reaction at a relatively low temperature in a shortened period of time as compared with conventional processes. It is considered that this is related to prevention of undesired side reactions such as severance of cellulose main chain or prevention of thermal degradation owing to blocking. thus contributing to improvement in physical properties of the filxs of the obtained CMEC.

After the completion of the etherification, the reaction mixture is cooled, most of the solvent is recovered by distillation and then CMEC is isolated by adding water and an acid to precipitate CMEC, filtering and drying CMEC.

In the second step of the process of the present invention, CMEC obtained in the 1st step is depolymerized to give CMEC whose solution is low in viscosity (hereinafter referred to as "depolymerized CMEC" or "low viscosity CMEC")

It is disclosed in U.S. Pat. No. 4,250,305 that the depolymerization of CMEC is conducted by adding hydrogen peroxide to a solution of CMEC dissloved in a water-alcohol mixed solvent and refluxing the solution. However, such a reaction system is under an acidic condention of about pH 4, and accordingly the change in quality as mentioned before is easy to occur. The second step in the present invention provides an improved technique not causing such a quality change. That is to say, according to the present invention, CMEC can be easily depolymerized without forming ester linkage by dissolving CMEC in an aqueous solution of a basic compound and adding a peroxide to the solution. Moreover, it is possible to control the affinity of the depolymerized CMEC for solvents by selecting the basic compound to be used.

Preferable examples of the basic compounds used in the depolymerization of CMEC are, for instance, ammonia, water-soluble amines such as monoethylamine, dimethylamine, methanolamine, benzylamine and cyclopropylamine, and alkali metal hydroxides. The basic compounds may be used alone or in admixture thereof.

In case that the desired viscosity of the product is low, or from the view of intending to reduce the amount of the peroxide required in depolymerization, the use of ammonia alone, a water-soluble amine alone or a system containing at least one of ammonia and the amine is advantageous, since the depolymerization is accelerated and the desired low viscosity CMEC can be obtained under milder conditions. The amount of the basic compound is not particularly limited so long as it is sufficient for solubilizing CMEC in water. Preferably, the basic compound is employed in an amount of 1 to 2 equivalents to the carboxyl groups included in CMEC.

The dissolution of CMEC can be easily made by dispersing CMEC in water, adding an aqueous solution of the basic compound to the dispersion and agitating it. Of course, a water-soluble salt of CMEC and a base can be used in the form of an aqueous solution instead of dissolving CMEC in water by using the basic compound.

Any water-soluble peroxides can be used in the depolymerization, but from the industrial point of view, hydrogen peroxide is preferable. The amount of the peroxides varies depending on the viscosities (molecular weights) of the starting material and the product, the depolymerization temperature and the kind of the basic compound used. Usually, the peroxides are employed in an amount of 1 to 30% by weight based on CMEC, and it is desirable to select other reaction conditions on the basis of the amount of the peroxides. When the amount of the peroxides is less than 1% by weight, not only the depolymerization efficiency is bad, but also the product is easy to become insufficient in bleaching. When the amount is more than 30% by weight, there is a possibility that undesirable lowering of quality owing to oxidation occurs. In a like manner, the temperature and time of the depolymerization vary depending on the viscosities of the starting material and the product and the kinds and amounts of the peroxide and the basic compound, and cannot be unqualifiedly determined. In general, it is desirable to carry out the depolymerization at a temperature of from room temperature to 80° C., especially 30° to 60° C., for 0.5 to 24 hours.

The low viscosity CMEC obtained by depolymerizing CMEC up to the desired viscosity according to the above-mentioned conditions is present in the form of an aqueous solution of a water-soluble basic salt. For obtaining the depolymerized CMEC as the carboxylic acid type, it is necessary to subsequently carry out neutralization followed by solid-liquid separation. It is important to prevent the deterioration of quality in this third step as much as possible. For this puprpose, it is desired to make the treating conditions in the third neutralization-solid liquid separation step as mild as possible.

That is to say, any acids stronger than the cellulose derivative, namely the depolymerized CMEC in the form of a salt, are usable in the neutralization, and can be arbitrarily selected, for instance, from inorganic acids such as sulfuric acid and hydrochloric acid, and organic acids such as formic acid and acetic acid. A hydrogel obtained by the neutralization is heated at a temperature of not less than the dehydration temperature for the hydrogel, preferably from 60° to 90° C. more preferably not more than 80° C., thereby depositing the low viscosity oxycarboxylic acid type cellulose derivative, and the solid-liquid separation is then conducted. The system from the neutralization to the dehydration treatment is weakly acidic, and it is important to conduct the procedures at a low temperature in a short period of time as much as possible for preventing the quality change. For this purpose, it is preferable to conduct the neutralization in the presence of a lower alkyl alcohol having 1 to 3 carbon atoms or acetone, and is effective for lowering the dehydration temperature and shortening the dehydration time. Also, the use of these dehydration accelerators is effective not only for making the dehyration conditions mild, but also for making the particle size of the product large. It is possible to obtain the product having a particle size of not less than 1 mm by selecting the condition, and this is effective particularly in the case where the granulation is desired.

When the depolymerization is carried out according to the process of the present invention, it is possible to obtain a low viscosity CMEC having a different affinity for a solvent. That is to say, in investigation on the composition of the basic compound used in the depolymerization and the solvent affinity of the product, it has been found that in case of using ammonia or a water-soluble amine in a large quanitity as the basic compound, the affinity for water is increased, and in case of using an alkali metal hydroxide in a large quantity, the affinity for a nonaqueous solvent is increased. The reason is considered to be that the conformation in the solution of CMEC varies depending on the kind of the basic compound, and in its turn the state of distribution of hydrophilic group and hydrophobic group in the solid product obtained by the neutralization-dehydration treatment varies. Accordingly, the solvent affinity of the product can be freely controlled by adjusting the composition of the used basic compounds, namely the mixing ratio of ammonia or the water-soluble amine compound to the alkali metal hydroxide.

For instance, in case of using CMEC as an enteric coating material, a nonaqueous organic solvent such as a dichloromethane-methanol mixed solvent or a dichloromethane-ethanoal mixed solvent has hitherto been generally employed. When the product suited for such an enteric coating system is desired, the object can be attained by using an alkali metal hydroxide alone or a mixture of a major amount of an alkali metal hydroxide and a minor amount of ammonia or a water-soluble amine as the basic compound in the depolymerization of CMEC. On the other hand, in recent years, an aqueous enteric coating composition is demanded from the viewpoint of the safety against organic solvents. When the product suited for the aqueous enteric coating system is desired, the object can be attained by using ammonia or the water-soluble amine alone or a mixture of a major amount of ammonia or the water-soluble amine and a minor amount of the alkali metal hydroxide as the basic compound.

The CMEC obtained through the depolymerization in the 2nd step and the isolation in the 3rd step is very low in degree of change in quality owing to esterification (degree of esterification), and accordingly it is a low viscosity CMEC having an excellent stability in quality containing no insoluble gel material. The product of the present invention forms a film which has a high quality and does not cause change in quality, from a solution or dispersion thereof in suitable solvents, and is very useful as an enteric coating material for medicines.

CMEC which has been given a quality change due to esterification can be purified by dissolving CMEC in an aqueous solution of a basic compound, allowing to stand, neutralizing the solution under mild conditions, heating the resulting gel, and then filtering and washing the obtained powder with water according to the manners of the 2nd and 3rd steps in the present invention so as to hydrolyze the esterified portion. Of course, it is desirable to make the reaction not so as to cause quality change owing to esterification rather than purification of deteriorated CMEC.

In case of using the low viscosity CMEC of the present invention in the form of an organic solvent solution, the wet CMEC obtained in the 3rd step is dried. The product is a particulate CMEC which has a particle size of about 0.5 to about 5 mm and a good solubility and is easy to handle. When it is desired to obtain CMEC having a good dispersibility in water and being suitable for an aqueous enteric coating use, the wet CMEC obtained in the 3rd step is pulverized in the wet state and then dried. Even if water is added to the CMEC dried once and it is then subjected to pulverization, CMEC having a good dispersibility in water is not obtained.

Known grinders such as ball mill, Szegvari's attriter, disper mill, colloid mill and vibrating mill can be employed in the wet pulverization. The concentration of the solid matter in the wet pulverization varies depending on the kind of grinder and the desried particle size of the pulverized CMEC, but is usually at most 50% by weight, especially at most 30% by weight. Since the particle size of the wet-pulverized CMEC has an influence on the dispersibility in water of the obtained dry CMEC powder and in its turn on the film-forming property of an aqueous dispersion thereof, it is preferable to be as small as possible, usually at most 100 $\mu$m, especially at most 40 $\mu$m, more especially at most 10 $\mu$m.

The wet-pulverized CMEC is dried in a conventional manner, e.g. through-flow drying, vacuum drying, spray drying and freeze drying. Also, when the water content of the slurry is previously decreased, for instance, by heating and filtering the slurry to remove water before drying. the drying is easily conducted. Since CMEC is subject to the quality change owing to esterification under an acidic or neutral condition and the enteric property is affected thereby, it is preferable to make the treatment between the wet pulverization and the drying at a temperature as low as possible and in a time as short as possible.

In the drying step conducted after the wet pulverization, the oxycarboxylic acid type cellulose derivative, namely the low viscosity CMEC, obtained according to the process of the invention causes secondary agglomeration for reasons such that water acts as a binder, and is in an agglomerated form even after the drying. Accordingly, it has the features that there is no problem of dusting which is one of the defects of dry pulverization such as jet milling and moreover the redispersibility into water is very excellent.

It goes without saying that the CMEC obtained by the process of the invention has a solubility characteristic required for the enteric protective coating, namely a sufficient resistance to gastric juice and a sufficient solubility in intestinal juice, its film has excellent mechanical properties and accordingly the enteric coating film made thereof does not cause cracking. This property of the film can be estimated by the following substitute characteristics. That is to say, it can be estimated according to whether various characteristics measured under conditions mentioned after fall within the following ranges.

(1) Area shrinkage at the time of casting: at most 10%
(2) Tensile strength: at least 200 kg/cm$^2$
(3) Elongation: at least 3%

The area shrinkage at the time of casting, tensile strength and elongation are defined as follows:

Area shrinkage

CMEC showing a solution viscosity of 15±3 cP is dissolved in a methylene chloride-ethanol mixed solvent (50:50 by weight) to give a 5% by weight solution. The solution is cast onto a laboratory dish filled with mercury at 20° C. and 65% RH. The area of the obtained film (about 100 $\mu$m in thickness) is measured. The percentage of reduction of the film area to the dish area is defined as area shrinkage at the time of casting.

Tensile strength and elongation

The tensile strength and elongation of the cast film obtained according to the above-mentioned method are measured in a usual manner at 20° C. and 65% RH and at a tension speed of 5 mm/min. employing a tensile testing machine (Tensilon UTM-4100 type made by Toyo Baldwin Co., Ltd.) and a test specimen having a size of 10 mm×50 mm.

The process of the present invention scarcely produces insoluble material due to side reaction such as esterification. Even if the produced CMEC contains a slight amount of an insoluble material, since the process of the present invention includes a step which acts to remove it by hydrolysis of an ester portion, the finally obtained CMEC does not contain such a factor which exerts an influence upon solubility, formation of continuous film and enteric property. This property can be estimated by the degree of change in quality owing to esterification (degree of esterification). According to the process of the invention, it is possible to prepare CMEC having a degree of esterification of at most 5%, especially at most 2%, more especially at most 0.5%, whereas the degree of esterification of a conventional CMEC is about 10% or higher. The following effects are produced by this feature of the invention.

1. The solubility in solvents used for coating is improved.
2. In case that CMEC is dissolved in coating solvents, the viscosity of the solution is lower than that of a solution of a conventional CMEC having the same concentration and, therefore, the application property is improved.
3. The film-forming property is improved, and the film has improved characteristics. Accordingly, the first fluid resistance (resistance to a simulated gastric fluid) is improved, the necessary minimum coating amount is reduced. and cracking of a coating film is prevented. The superiority in film-forming property is also estimated by the fact that the minimum film-forming temperature is low.
4. Since the effective carboxyl group is increased. it is effective for improving the enteric property.

The degree of quality change owing to esterification (degree of esterification) q%, is determined according to the following equation.

$$q\% = \frac{p - r}{p} \times 100$$

wherein p is a content (%) of carboxyl group measured by an indirect titration method, and r is a content (%) of carboxyl group measured by a direct titration method.

The indirect titration is conducted with 0.1N H$_2$SO$_4$ with respect to an aqueous 0.1N NaOH solution of CMEC. The direct titration is conducted with 0.1N NaOH with respect to a solution of CMEC in an ethanol-water mixed solvent (8:2 by weight). In both cases, phenolphthalein is used as an indicator.

The process of the present invention can eliminate the defects of a conventional art and moreover can economically provide CMEC easily dispersible in water, and accordingly its industrial significance is very large.

A method of preparing an enteric coating liquid by dissolving the CMEC obtained by the process of the invention in a solvent or dispersing it in water is not particularly limited. At the time of preparing the enteric coating liquid or after the preparation, if necessary, there may be added various additives for further improving the dispersion stability, film-forming property, etc., e.g. various emulsifiers; film-forming assistants for raising the film-forming property such as hydroxypropyl methyl cellulose, hydroxypropyl cellulose, polyvinyl alcohol, polyvinyl acetate and acrylic copolymers; plasticizers such as polyethylene glycol, ethylene glycol, triacetin and various glycerin fatty acid esters; alkali metal salts of acids having an acid dissociation constant pKa of at least 3 at 25° C.; and coloring agents such as food dye.

The present invention is more specifically described and explained by means of the following Examples in which all parts and % are by weight unless otherwise noted. It is to be understood that the present invention is not limited to the Examples, and various changes and modifications may be made in the invention without departing from the spirit and scope thereof.

In the Examples, values of measurement are those measured by the before-mentioned methods and the following methods.

(1) Viscosity

A sample was dissolved in an ethanol-water mixed solvent (80:20 by weight) to give a 5% solution. The viscosity was measured at 25° C. and at 30 r.p.m. in the number of rotations of a rotor by using a Brookfield viscometer.

(2) Viscosity ratio

At the time of measuring the viscosity, the viscosity was measured at 30 r.p.m. ($\eta_{30}$) and at 6 r.p.m. ($\eta_6$). The viscosity ratio is defined as $\eta_6/\eta_{30}$. It is considered that the larger the viscosity ratio, the association of polymer molecules occurs more easily in the solvent, that is to say, the more the affinity for the solvent is lowered.

(3) Minimum film-forming temperature (hereinafter referred to as "MFT")

To a homogenizer (made by Tokushu Kika Kogyo Kabushiki Kaisha) were added 0.294 part of sodium citrate, 0.017 part of citric acid, an emulsifier (commercial name "Tween 80" made by Kao Atlas Kabushiki Kaisha), 5 parts of a 2% aqueous solution of hydroxypropyl methyl cellulose (commercial name "TC-5R" made by Shin-Etsu Chemical Co. Ltd.), 3 parts of a plasticizer (a fatty acid glyceryl ester composed mainly of caprylic acid monoglyceride, commercial name "MGK" made by Nikko Chemicals Kabushiki Kaisha), 10 parts of a sample CMEC sieved to obtain sieve fractions between 70 and 16 meshes and 106.6 parts of water. They were dissolved or dispersed at room temperature. The obtained dispersion was passed through a 70 mesh sieve, and using the obtained filtrate, MTF was measured according to a usual method.

(4) Non-dispersion percentage

The dispersion prepared by the method in the above item (3) was passed through a 70 mesh sieve. The content of coarse particles having a particles size of not less than 70 meshes was obtained and it is defined as the non-dispersion percentage.

(5) Preparation of tablets used for a coating test (a) Tablets for a nonaqueous coatinq liquid A mixture of microcrystalline cellulose (commercial name "Avicel" made by Asahi Kasei Kogyo Kabushiki Kaisha) and rapid disintegrative vehicle (hydroxypropyl starch commercially available under commercial name "Perfiller" from Freund Industry Co., Ltd.) in a weight ratio of 1:1 was directly compressed to give a tablet having a weight of 200 mg and a diameter of 8 mm.

(b) Tablets for an aqueous coatinq liquid

An 8% aqueous solution of hydroxypropyl methyl cellulose ("TC-5R" made by Shin-Etsu Chemical Co., Ltd.) was sprayed on the tablet prepared in the above item (5)-(a) to form a coating film in an amount of about 2.5% based on the tablet).

(6) Preparation of coating liquid (a) Nonaqueous coatinq liquid

A coating liquid was prepared by dissolving 1 part of CMEC and 0.1 part of acetylated monoglyceride (commercial name "Myvaset 9-40T" made by Eastman Kodak Company) in 11.5 parts of a methylene chloride/ethanol mixed solvent (1:1 by weight).

(b) Aqueous coatinq liquid

An aqueous dispersion prepared in the same manner as in the above item (3) was used as an aqueous coating liquid.

(7) Coating procedure and estimation (a) Coating of nonaqueous coating liquid

An automatic film coating apparatus (FM-II type made by Freund Industry Co., Ltd.) was charged with 1 kg of the above-mentioned tablets, and the above nonaqueous coating liquid (6)-(a) was sprayed at a rate of about 8 ml/minute onto the tablets to form a coating film in an amount of about 8% based on the tablet, during which a coating pan was rotated at 14 r.p.m. and the coating was dried with dry hot air at a temperature of 60° to 70° C. After the completion of the coating, the film was further dried with the same hot air as above for 20 minutes. The state of the film on the surface of the tablet such as presence of cracks was observed by the nacked eye and further with a scanning type electron microscope in a usual manner. Further, the enteric property was estimated by a disintegration test.

(b) Coating of aqueous coatinq liquid

The automatic film coating apparatus was charged with 0.35 kg of the above-mentioned tablets, and the above aqueous coating liquid (6)-(b) was sprayed at a rate of about 5 ml/minute onto the tablets to form a coating film in an amount of about 12% based on the tablet, during which the coating pan was rotated at about 32 r.p.m. and the coating was dried with dry hot air at a temperature of 80° to 85° C. After the completion of the coating, the film was further dried with the dry air for 20 minutes. The obtained enteric coated tablet was subjected to a disintegration test to estimate the enteric property.

(8) Disintegration test

The disintegration test was made by employing test fluids provided in Pharmacopedia of Japan (10th edition).

In a 1st fluid (simulated gastric fluid) of pH about 1.2 prepared by using diluted hydrochloric acid and sodium chloride was immersed the coated tablet for 120 minutes. With respect to the non-disintegrated tablet, the tablet was further immersed in a 2nd fluid of pH about 6.8 (simulated intestinal fluid) which was a dislute aqueous solution of NaOH and $KH_2PO_4$, and the time up to disintegration was measured.

EXAMPLE 1

(Step 1)

In an autoclave, 84.7 g of CMC having a degree of substitution (hereinafter referred to as "DS") of carboxymethyl group of 0.42, a viscosity ratio $\eta_6/\eta_{30}$ of 1.120 and a water content of 5.6% was dispersed in 320 g of toluene. After adding 71.1 g of a 48% aqueous solution of sodium hydroxide to the dispersion at a temperature of 30° to 40° C. with agitation, 51.1 g of flaky sodium hydroxide was added and the dispersion was further thoroughly agitated at a temperature of 35° to 45° C. for 10 minutes to give a slurry.

To the slurry were added 5.9 g of trimethylamine in the form of a 30% aqueous solution and 204 g of ethyl chloride. and the reaction was carried out at a temperature of 115°±5° C. for 10 hours. The reaction system was in a good slurry state throughout the reaction.

After cooling the reaction mixture, most of the solvent was recovered by distillation, and about 200 g of water was added to the residue. The system was adjusted to pH about 1 with 12N sulfuric acid, washed with water and dried to give CMEC.

(Step 2)

In 610 parts of water was dispersed 50 parts of CMEC obtained in the 1st step having a DS of carboxymethyl group of 0.42, a DS of ethoxyl group of 2.10, a viscosity of 80.4 cP and a degree of esterification of 7.4%, and 8.4 parts of 25% aqueous ammonia was added, and CMEC was dissolved at room temperature. After completely dissolving CMEC, 2.5 parts of a 30% aqueous solution of hydrogen peroxide was added to the solution, and it was agitated at a temperature of 50° to 55° C. for 6.1 hours.

(Step 3)

The reaction mixture was then cooled to room temperature, and after adding 50 parts of isopropyl alcohol, 1.8N sulfuric acid was added to the system up to pH 3.0 to give a hydrogel.

The hydrogel was heated with agitation. At about 60° C., the dehydration began and solid particles began to precipitate. After further elevating the temperature to 70° C., the system was kept for 5 minutes at that temperature. It was then filtered in the hot state with suction using a Büchner funnel, and sufficiently washed with hot water of 70° C.

(Step 4-1)

The washed product was dried with hot air at 70° C. to give a granulated low viscosity CMEC having a particle size of 2 to 3 mm. The low viscosity CMEC had a DS of carboxymethyl group of 0.42, a DS of ethoxyl group of 2.10, a viscosity of 13.1 cP, an area shrinkage of 3.2%, a tensile strength (film) of 287 kg/cm², an elongation (film) of 3.3% and a degree of esterification of 0.2%. At the time of dissolution, no gel impurity was observed.

(Step 4-2)

To 50 parts of the wet CMEC (water content: 54%) obtained in the above step 3 was added 50 parts of water, and CMEC was pulverized to particles having an average particle size of 20 μm by a ball mill. The particles were then dried in a through-flow drier at 70° C. to give aggregated CMEC.

The aggregate was crushed to particles of 70 to 16 meshes. The aqueous dispersion thereof prepared by the before-mentioned MFT measuring method had a MFT of 32° C. Also, the degree of esterification was 0.5% and the non-dispersion percentage was 0.2%, and the DS and viscosity were the same as those of the low viscosity CMEC obtained in the above step 4-1. The obtained low viscosity CMEC showed good dispersibility in water and film-forming property.

The disintegration test was made by employing the obtained low viscosity CMEC. No change was observed in the test with the first fluid, and in the test with the second fluid. the coating was completely disintegrated in 7 to 9 minutes. Thus, it was confirmed that the product of the present invention could provide a good aqueous enteric coating material.

On the other hand, the low viscosity CMEC obtained in the above step 4-1 was pulverized to particles having a particle size of 70 to 16 meshes, and dispersed in water according to the before-mentioned MFT measuring method. The thus prepared aqueous dispersion had a MFT of higher than 70° C., a non-dispersion percentage of 25%, and accordingly was insufficient in dispersibility and film-forming property.

EXAMPLE 2

CMEC was prepared in the same manner as in step 1 of Example 1.

CMEC was depolymerized by mixing 50 parts of CMEC, 650 parts of water and 5 parts of particulate NaOH (purity: 97%) at room temperature to dissolve CMEC, adding 2.5 parts of a 30% aqueous solution of hydrogen peroxide to the resulting solution and agitating at a temperature of 50° to 55° C. for 5.8 hours.

Thereafter, the procedures of the step 3, step 4-1 and step 4-2 in Example 1 were repeated.

The CMEC obtained in step 4-1 had a DS of carboxymethyl group of 0.42, a DS of ethoxyl group of 2.10, a viscosity of 18.0 cP, an area shrinkage of 5.2%, a tensile strength (film) of 255 kg/cm², an elongation (film) of 3.1% and a degree of esterification of 0.1%. No insoluble gel material was observed at the time of dissolution.

The CMEC obtained in step 4-2 had a MFT of 35° C., a non-dispersion percentage of 0.0% and a degree of esterification of 0.4. In the disintegration test, no change was observed against the first fluid, and complete disintegration was observed in 8 to 11 minutes in the test with the second fluid. Thus, it was confirmed that the product was useful as an enteric coating material for an aqueous system.

EXAMPLE 3

(Step 1)

In an autoclave, 84.7 g of CMC having a DS of carboxymethyl group of 0.48, a viscosity ratio $\eta_6/\eta_{30}$ of 1.050 and a water content of 5.6% was dispersed in 320 g of toluene. While maintaining at a temperature of 30° to 40° C. with agitation, 71.1 g of a 48% aqueous solution of sodium hydroxide and 51.1 g of flaky sodium hydroxide were added to the dispersion in that order, and it was further agitated at a temperature of 35° to 45° C. for 10 minutes to give a slurry.

To the slurry were added 3.4 g of tetraethylammonium chloride and 204 g of ethyl chloride, and the reaction was conducted at a temperature of 115°±5° C. for 10 hours. The reaction system was in a good slurry state throughout the reaction.

After cooling the reaction mixture, most of the solvent was recovered by distillation, about 200 g of water was added to the residue, and the system was adjusted to pH about 1 with 12N sulfuric acid and washed with water to give CMEC. The obtained CMEC had the following characteristics. Viscosity: 30.0 cP, DS of ethoxyl group: 2.01, DS of carboxymethyl group: 0.48, Degree of esterification: 6.2%

(Step 2)

In 606.7 parts of water was dispersed 50 parts of CMEC obtained in step 1, and 8.4 parts of 25% aqueous ammonia and 1.66 parts of sodium hydroxide were added, and CMEC was completely dissolved at room temperature. After completely dissolving CMEC, the temperature was elevated to 50° C. and 2.5 parts of a 30% aqueous solution of hydrogen peroxide was added to the solution, and it was agitated at a temperature of 50° to 55° C. for 5.5 hours.

(Step 3)

The reaction mixture was then cooled to room temperature, and after adding 10 parts of isopropyl alcohol, 3.6N sulfuric acid was added to the system up to pH 3.0 to deposit a solid matter. It was heated to 80° C. and kept for 5 minutes at that temperature. It was then filtered in the hot state with suction using a Büchner funnel, and sufficiently washed with hot water of 70° to 80° C. to give wet CMEC having a particle size of 1 to 2 mm and a water content of 50%.

(Step 4-1)

The wet CMEC was dried with hot air at 70° C. to give CMEC having a particle size of 1 to 2 mm. The characteristics of the obtained CMEC were as follows: DS of carboxymethyl group: 0.48, DS of ethoxyl group: 2.01 Viscosity: 12.5 cP, Degree of esterification: 0.0%, Area shrinkage: 0.7%, Tensile strength: 230 kg/cm$^2$, Elongation: 4.0%. At the time of dissolution, no insoluble gel material was observed.

(Step 4-2)

The CMEC obtained in the above step 3 was pulverized to particles having an average particle size of 30μm by a ball mill. The particles were then dried in a through-flow drier at 70° C. to give aggregated CMEC.

The aggregate was crushed to particles of 70 to 16 meshes. The crushing was conducted without dusting. The aqueous dispersion thereof prepared by the beforementioned MFT measuring method had a MFT of 27° C. Also, the degree of esterification was 0.32% and the nondispersion percentage was 0.0%. The thus obtained low viscosity CMEC showed good dispersibility in water and film-forming property.

The disintegration test was made by employing the obtained low viscosity CMEC. No change was observed in the test with the first fluid, and in the test with the second fluid, the coating was completely disintegrated in 8 to 10 minutes. Thus, it was confirmed that the product of the present invention could provide a good aqueous enteric coating material.

EXAMPLE 4

To 50 parts of the depolymerized CMEC obtained in step 3 of Example 3 having a particle size of 1 to 2 mm and a water content of 50% was added 50 parts of water. and CMEC was pulverized to particles having an average particle size of 4.0 μm by a vibrating mill (B-1 type made by Chuo Kakoki Shoji Kabushiki Kaisha). The resulting slurry was heated to 80° C. and filtered with suction by a Büchner funnel to give a CMEC cake having a solid content of 53%.

The cake was dried at 70° C. in a through-flow drier to give massive depolymerized CMEC of which the viscosity was 12.4 cP. It was then crushed to particles having a particle size of 70 to 16 meshes. The aqueous dispersion of the depolymerized CMEC particles prepared by the MFT measuring method had a MFT of not more than 27° C. Also, the depolymerized CMEC had a non-dispersion percentage of 0.0%, a degree of esterification of 0.02%, and the dispersibility and the film-forming property were good.

Since water was previously removed from the wet-crushed CMEC slurry by filtration and then drying was conducted, the drying time was shortened to about ¼ of the drying time required in the case of not conducting the filtration, namely to 3 hours. As a result, the change in quality during the crushing and drying could be prevented.

In the disintegration test, no change was observed against the first fluid, and complete disintegration was observed in 8 to 12 minutes in the test with the second fluid. Thus, it was confirmed that the product was useful as an enteric coating material for an aqueous system.

EXAMPLE 5

The procedures of the steps 1, 2, 3 and 4-1 in Example 3 were repeated except that the basic compound used in the step 2 was changed as shown in Table 1, and also in the step 3, 50 parts of isopropyl alcohol and 1.8N sulfuric acid were employed and the maximum dehydration temperature was 70° C.

The properties of the obtained CMEC are shown in Table 1.

In Table 1, CMEC used for the aqueous coating system is those having a particle size of about 10 μm obtained by pulverizing the dry CMEC obtained in the step 4-1.

TABLE 1

| Run No. | 1 | 2 | 3 | 4 |
|---|---|---|---|---|
| Basic compound (part) | | | | |
| 25% Aqueous ammonia | 8.4 | 8.4 | 8.4 | — |
| NaOH (purity: 97%) | — | 1.66 | 3.32 | 4.91* |
| Ammonia/NaOH ratio | — | 1/0.33 | 1/0.67 | — |
| Properties | | | | |
| Viscosity | 14.5 | 12.5 | 13.0 | 20.0 |
| Viscosity ratio | 1.01 | 1.03 | 1.07 | 1.12 |
| Degree of esterification | 0.2 | 0.1 | 0.1 | 0.0 |
| MFT (°C.) | <27 | 32 | 38 | 42 |
| Insoluble gel material | none | none | none | none |
| Aqueous coating system | | | | |
| Application property | slight dusting | — | — | slight dusting |
| First fluid | pass | — | — | failure |

TABLE 1-continued

| Run No. | 1 | 2 | 3 | 4 |
|---|---|---|---|---|
| disintegration test | | | | (disintegration in 100 min.) |
| Second fluid disintegration test | disintegration in 4-6 min. | — | — | — |
| Film-forming property | even film | — | — | uneven film |
| Solvent coating system | | | | |
| Application property | slight dusting | — | — | good |
| First fluid disintegration test | pass | — | — | pass |
| Second fluid disintegration test | disintegration in 8-10 min. | — | — | disintegration in 4-5 min. |
| Film-forming property | nearly even film | — | — | even film |

*50 parts of water was added.

The viscosity ratio of the solutions of the obtained CMEC products increases with increasing the amount of NaOH used in the depolymerization. This fact indicates that the affinity for a solvent of the product is changed by changing the composition of the basic compound mixture used in the depolymerization, in other words, that the affinity for a nonaqueous solvent is increased by increasing the content of NaOH and the affinity for an aqueous solvent is increased by decreasing the content of NaOH. In fact, the smaller the NaOH content, the lower the MFT of an aqueous dispersion of CMEC and the hydrophilic property of CMEC is more increased.

Also, from the results of the aqueous coating wherein the CMEC particles obtained by pulverizing dry CMEC are used, it is understood that in case of the depolymerized CMEC obtained by using a major amount of NaOH in the depolymerization, mere mechanical pulverization does not provide a CMEC suitable for aqueous coating.

COMPARATIVE EXAMPLE 1

To 450 parts of a 80% aqueous solution of methanol was added 70 parts of the CMEC obtained in step 1 of Example 3, and was dissolved under reflux with agitation. To the resulting solution was added 7 parts of a 30% aqueous solution of hydrogen peroxide, and the depolymerization was carried out at a temperature of 50° to 55° C. for 5.5 hours. At that time, the reaction system was acidic, namely pH about 4. From the reaction mixture, 300 parts of the reaction solvent was then recovered by distillation under ordinary pressure, and 250 parts of water was added to the residue, and the distillation was further continued to recover the solvent until the inner temperature reached 98° C. The precipitated low viscosity CMEC was filtered with suction by a Büchner funnel, washed sufficiently with hot water of 70° C. and dried with hot air at 70° C. The thus obtained low viscosity CMEC had a degree of esterification of 12.1% and contained an insoluble gel material. Also, the viscosity was 14.2 cP.

COMPARATIVE EXAMPLE 2

The procedure of Comparative Example 1 was repeated. After dispersing 50 parts of the obtained low viscosity CMEC in 661.7 parts of water, 4.98 parts of a 97 NaOH was added to the dispersion and the CMEC was dissolved at room temperature to give a uniform solution.

Isopropyl alcohol was added to the solution, and the neutralization and dehydration were carried out in the same manner as in step 3 of Example 3 to purify the low viscosity CMEC. The viscosity and the degree of esterification of the purified CMEC were 12.8 cP and 2.8%, respectively.

The degree of esterification is decreased from 12.1% to 2.8% by the alkali treatment. However, the degree of esterification of the purified CMEC is still higher in spite of the two step procedure of depolymerization and alkali treatment than that of the low viscosity CMEC obtained in Example 3. It is clear that the process of the present invention is superior to a conventional process in that the process is simple because of no necessity of isolation of the depolymerized CMEC followed by the purification and in that the quality is better.

It is understood that the depolymerization technique in the process of the present invention is superior in providing a low viscosity CMEC of high quality having a controlled affinity for solvents as compared with a conventional depolymerization of a high viscosity CMEC under acidic condition.

EXAMPLE 6

(Step 1)

In an autoclave, 85.1 g of CMC having a DS of carboxymethyl group of 0.61, a viscosity ratio $\eta_6/\eta_{30}$ of 1.105 and a water content of 6.0% was dispersed in 400 g of toluene. To the dispersion was added 204 g of a 48% aqueous solution of sodium hydroxide at a temperature of 30° to 40° C. with agitation, and the dispersion was further thoroughly agitated at a temperature of 35° to 45° C. for 10 minutes to give a slurry.

To the slurry were added 5.6 g of benzylamine and 176 g of ethyl chloride, and the reaction was carried out at a temperature of 115°±5° C. for 10 hours. The reaction system was in a good slurry state throughout the reaction.

After cooling the reaction mixture, the post-treatment was carried out in the same manner as in step 1 of Example 3 to give CMEC having the following characteristics: viscosity 82 cP, DS of carboxymethyl group 0.61, DS of ethoxyl group 2.08 and degree of esterification 8.0%.

(Steps 2, 3 and 4-1)

The procedures of steps 2 to 4-1 in Example 3 were repeated to give CMEC particles of 2 to 3 mm in particle size having the following characteristics: viscosity 15.9 cP, DS of ethoxyl group 2.08, DS of carboxymethyl group 0.61, degree of esterification 0.3%. area shrinkage of 0.0%, tensile strength 220 kg/cm² and elongation 4.2%.

(Step 4-2)

To 50 parts of the depolymerized CMEC (particle size: 2 to 3 mm. water content: 55%) obtained in the step 3 was added 50 parts of water, and the CMEC was wet-pulverized to particles having an average particle size of 10 μm by a micronizer. The particles were then dried in a through-flow drier at 70° C. to give aggregated CMEC (viscosity: 12.5).

The aggregate was crushed to particles of 70 to 16 meshes. The aqueous dispersion thereof prepared by the MFT measuring method had a MFT of below 27° C. Also, the degree of esterification was 0.28% and the nondispersion percentage was 0.0%, thus the obtained low viscosity CMEC showed good dispersibility in water and film-forming property.

The disintegration test was made by employing the obtained low viscosity CMEC. No change was observed in the test with the first fluid, and in the test with the second fluid, the coating was completely disintegrated in 7 to 11 minutes. Thus, it was confirmed that the product of the present invention could provide a good aqueous enteric coating material.

On the other hand, the low viscosity CMEC obtained in the step 3 was dried at 70° C. in a throughflow drier without wet-pulverizing, and the obtained mass was pulverized to particles having a particle size of 70 to 16 meshes. The aqueous dispersion prepared according to the MFT measuring method had a MFT of higher than 70° C. and a non-dispersion percentage of 15%, and accordingly it was insufficient in dispersibility and film-forming property.

COMPARATIVE EXAMPLE 3

Mercerization was carried out by immersing 84.7 g of the same CMC as used in Example 1 in 400 g of a 48% aqueous solution of sodium hydroxide and maintaining at 25° C. for 20 hours. The resulting mercerized CMC was squeezed by a squeezer until the squeeze ratio (weight ratio of the squeezed mercerized CMC to the used CMC) reached 3.7 to adjust the contents of sodium hydroxide and water.

The mercerized CMC, 400 g of toluene, 3.4 g of tetraethylammonium chloride and 204 g of ethyl chloride were placed in an autoclave, and the reaction was carried out at a temperature of 115°±5° C. for 21 hours with vigorous agitation. The reaction system was in a good slurry state throughout the reaction.

After cooling the reaction mixture, it was subjected to the depolymerization and the post-treatment in the same manner as in steps 2, 3 and 4-1 of Example 1 to give a purified CMEC having a DS of ethoxyl group of 2.18, a DS of carboxymethyl group of 0.42 and a solution viscosity of 13.8 cP (solution viscosity of the starting CMEC before depolymerization: 48 cP).

The thus obtained low viscosity CMEC had sufficient resistance to gastric juice and solubility in intestinal juice and also had a film strength of 360 kg/cm$^2$, but the area shrinkage and elongation were 30.8% and 2.1%, respectively, and were worse than those of the low vicosity CMEC of the present invention.

In addition to the ingredients used in the Examples, other ingredients can be used in the Examples as set forth in the specification to obtain substantially the same results.

What we claim is:

1. A process for preparing carboxymethyl ethyl cellulose suitable for enteric coating which comprises:
   (1) adding an alkali metal hydroxide to a dispersion of carboxymethyl cellulose in an organic solvent and subjecting the dispersion to a reaction with an ethyl halide in the presence of a phase transfer catalyst to produce carboxymethyl ethyl cellulose, said carboxymethyl cellulose having a degree of substitution of carboxymethyl group of 0.2 to 1.2, and said organic solvent being substantially immiscible with an aqueous solution of the alkali metal hydroxide and capable of dissolving the ethyl halide.
   (2) dissolving carboxymethyl ethyl cellulose in an aqueous solution of a basic compound selected from the group consisting of ammonia, a water-soluble amine and an alkali metal hydroxide, and subjecting the resulting solution to depolymerization in the presence of a peroxide,
   (3) neutralizing the resulting basic solution of the depolymerized carboxymethyl ethyl cellulose with an acidic substance in the presence of an alkyl alcohol having 1 to 3 carbon atoms or acetone to form a hydrogel of carboxymethyl ethyl cellulose, and subjecting the hydrogel to dehydration with agitation at a temperature not lower than the temperature at which dehydration occurs, followed by isolation and washing with water, and
   (4) drying the wet carboxymethyl ethyl cellulose.

2. The process of claim 1, wherein said phase transfer catalyst is a tetraalkylammonium salt provided that the alkyl means an alkyl group having 1 to 4 carbon atoms or an aralkyl group having 7 to 8 carbon atoms.

3. The process of claim 1, wherein said dehydration is carried out at a temperature of 60° to 90° C.

4. The process of claim 1, wherein said drying is carried out after pulverizing the wet carboxymethyl ethyl cellulose in the wet state.

5. The process of claim 4, wherein the pulverized carboxymethyl ethyl cellulose has an average particle size of not more than 100 μm.

6. The process of claim 1, wherein said basic compound is a mixture of an alkali metal hydroxide and at least one member selected from the group consisting of ammonia and a water-soluble amine.

* * * * *